United States Patent [19]

Ueda et al.

[11] Patent Number: 5,229,527

[45] Date of Patent: Jul. 20, 1993

[54] METHOD FOR PRODUCTION OF PHTHALIC ANHYDRIDE BY VAPOR-PHASE OXIDATION OF MIXTURE OF ORTHO-XYLENE WITH NAPHTHALENE

[75] Inventors: Kenji Ueda; Masaaki Okuno; Tatsuya Kawabata; Shinya Tanaka, all of Hyogo, Japan

[73] Assignee: Nippon Shokubai Co., Ltd., Osaka, Japan

[21] Appl. No.: 965,228

[22] Filed: Oct. 23, 1992

[30] Foreign Application Priority Data

Oct. 25, 1991 [JP] Japan .................................. 3-279895

[51] Int. Cl.$^5$ .......................................... C07D 307/89
[52] U.S. Cl. .................................................... 549/248
[58] Field of Search .......................................... 549/248

[56] References Cited

U.S. PATENT DOCUMENTS

| | | | |
|---|---|---|---|
| 4,472,587 | 9/1984 | Benedetti et al. | 549/248 |
| 4,855,458 | 8/1989 | Fuhrmann et al. | 549/248 |
| 4,879,387 | 11/1989 | Hara | 549/248 |

FOREIGN PATENT DOCUMENTS 1-190677  7/1989  Japan .................................. 549/248

*Primary Examiner*—Bernard Dentz
*Attorney, Agent, or Firm*—Omri M. Behr; Matthew J. McDonald

[57] ABSTRACT

The production of phthalic anhydride by the catalytic vapor-phase oxidation of a mixture of ortho-xylene and naphthalene is accomplished advantageously by a method which comprises packing in a reaction vessel, as a former-stage catalyst, a catalyst produced by supporting on an inactive carrier a catalytic substance composed of vanadium oxide and a specific anatase type titanium dioxide, Nb, P, Sb, and at least one component selected from the group consisting of K, Cs, Rb, and Tl as oxide and, as a latter-stage catalyst, a catalyst similar to the former-stage catalyst excepting the amount of the at least one component selected from among K, Cs, Rb, and Tl is in the range between 17 and 63% by weight as an oxide based on the amount of the same component used in the former-stage catalyst, both in specified bed heights feeding to this reaction vessel the mixture of ortho-xylene and naphthalene and a molecular oxygen-containing gas at a temperature in the range between 300° and 450° C.

12 Claims, 1 Drawing Sheet

METHOD FOR PRODUCTION OF PHTHALIC ANHYDRIDE BY VAPOR-PHASE OXIDATION OF MIXTURE OF ORTHO-XYLENE WITH NAPHTHALENE

BACKGROUND OF THE INVENTION

1. Field of the Invention

This invention relates to a method for the production of phthalic anhydride by the vapor-phase oxidation of a mixture of ortho-xylene with naphthalene. More particularly, it relates to a method for the production of phthalic anhydride by catalytic vapor-phase oxidation effected by introducing a mixture of ortho-xylene with naphthalene and a molecular oxygen-containing gas into a shell-and-tube type fixed-bed reactor packed with a specific catalyst.

2. Description of the Prior Art

As a means of producing phthalic anhydride from the mixture of ortho-xylene with naphthalene as a raw material, a method which, for example, uses a catalyst based on a vanadium-titanium dioxide composite (JP-A-58-74675) has been known to the art. The method disclosed in this patent publication comprises using a catalyst for oxidation of ortho-xylene until the catalyst has been deactivated through aging and then introducing naphthalene into the site of oxidation in proportion to the degree of deactivation. This introduction of naphthalene is effected particularly after the reaction of ortho-xylene only has continued for 50 months. This method remains inexecutable for a considerable time until the feed of the mixed raw material is able to start. Further, it does not allow selection of a mixing ratio of raw materials which is economically advantageous in the light of the existing situation of the supply of raw materials. This method cannot generally be embodied because it does not define the catalyst in terms of such factors as chemical composition.

An actual case of successful production of phthalic anhydride from a mixture of ortho-xylene and naphthalene of a freely selected ratio is reported in "Aromatics," Vol. 38, Nos. 9–10, pages 12–18 (1985). Again in this case, however, the production is performed after the reaction exclusively of naphthalene has been continued for one year. The report has no mention of the possibility of this method being performed from the outset of the reaction. It offers no detailed description of the catalyst to be used in the method and, therefore, does not allow identification of the catalyst.

U.S. Pat. No. 4,879,387 is known to have disclosed a catalyst composition and a method for the use thereof. It discloses a catalyst for the oxidation of naphthalene and also discloses working examples using a 50/50 mixture of ortho-xylene/naphthalene (Examples 3 and 27). It further discloses working examples for effecting a reaction solely of naphthalene with the same catalyst as already used for a reaction solely of ortho-xylene (Examples 26 and 10). Though this patent publication does contain a mention, to the effect that, naphthalene and ortho-xylene may be used as a mixed raw material, it does not show any measures which cope with changes in the hot spot (the spot of the highest heat in the catalyst bed) which occur in the use of the mixed raw material resulting from the difference in the mixing ratio.

The inventor of U.S. Pat. No. 4,879,387 mentioned above, relating to the production of phthalic anhydride by the use of a mixed raw material, offers a detailed description of a method for mixing the raw material in JP-A-1-190677. This patent publication, however, shows no restriction regarding the catalyst. A review of the working examples cited in this patent publication leads to an inference that the method disclosed is usable with all the mixing ratios ranging from 100% of ortho-xylene to 100% of naphthalene. The yields of produced phthalic anhydride indicated in these working examples, however, are considerably lower than those indicated in the working examples cited in U.S. Pat. No. 4,879,387.

As shown above, the catalyst which is usable for all mixing ratios must be capable of coping with changes in the mixing ratio by sacrificing yield or product as compared with a catalyst which is optimized for the mixed raw material having a fixed mixing ratio.

We have so far studied and developed catalysts for the production of phthalic anhydride by the oxidation of ortho-xylene and/or naphthalene (JP-A-56-73543, JP-A-56-78635, and JP-A-57-105241) to realize high productivity (high load and high selectivity) and long catalyst service life in a limited range of mixing ratios. When the conventional catalyst is used, the mixing ratio of the components of the mixed raw material mentioned above is limited to a narrow range. When the mixing ratio deviates from this range, the production entails numerous problems relating to the yield of phthalic anhydride produced, the quality of the product, and the service life of the catalyst. These problems are prominent particularly when the reaction of oxidation is carried out with a catalyst which is favorable for the oxidation of naphthalene and the proportion of ortho-xylene in the mixing ratio of ortho-xylene to naphthalene is not less than 50% or when the reaction is carried out with a catalyst which is favorable for the oxidation of ortho-xylene and the proportion of ortho-xylene in the mixing ratio of ortho-xylene to naphthalene is not more than 50%.

Specifically when the reaction is carried out with a catalyst which is favorable for the oxidation of naphthalene and the proportion of ortho-xylene in the mixing ratio of ortho-xylene with naphthalene is not less than 50%, the amount of phthalide, a substance conductive to adverse effects in the quality of the product, and which is generated in the reaction, increases notably.

Conversely, when the reaction is carried out with a catalyst which is favorable for the oxidation of ortho-xylene and the proportion of ortho-xylene in the mixing ratio of ortho-xylene to naphthalene is not more than 50%, the reaction temperature must be lowered to ensure a high yield of the reaction. Again in this case, the amount of naphthoquinone, a substance detrimental to the quality of the product and known to be generated, is increased. When the reaction temperature is heightened for the purpose of repressing the occurrence of this mischievous substance, the yield of phthalic anhydride is impaired and an abnormal hot spot occurs in the frontal part of the catalyst bed and produces an adverse effect on the service life of the catalyst. These problems are liable to gain further prominence when the catalyst is exposed to a high load.

An object of this invention, therefore, is to provide a novel method for the production of phthalic anhydride by vapor-phase oxidation of a mixture of ortho-xylene with naphthalene.

Another object of this invention is to provide a method which produces phthalic anhydride of high quality from a mixture comprising of ortho-xylene and naphthalene in a widely variable ratio over a long period even when the load exerted on the raw material is high and also provide a catalyst composition useful for the execution of the method.

SUMMARY OF THE INVENTION

These objects are accomplished by a method for the production of phthalic anhydride by the catalytic vapor-phase oxidation of a mixture of ortho-xylene and naphthalene with a molecular oxygen-containing gas by the use of a shell-and-tube type fixed-bed reactor, which method comprises packing in the reactor a former-stage catalyst in a bed height of 15 to 85% by volume of the total catalyst bed height from the raw material gas inlet side and a latter-stage catalyst in a bed height of 85 to 15% by volume of the total catalyst bed height from the raw material gas outlet side in the form of superposed layers, the former-stage catalyst being obtained by supporting a catalytic substance on an inactive carrier at a rate in the range between 5 and 20 g/100 ml, the catalytic substance comprising 1 to 20 parts by weight of vanadium oxide as $V_2O_5$ and 99 to 80 parts by weight of a porous anatase type titanium dioxide as $TiO_2$ having particle diameters substantially in the range between 0.4 and 0.7 μm and a specific surface area (BET surface area) in the range between 10 and 60 $m^2/g$ and further incorporating therein, based on 100 parts by weight of the total amount of the two components mentioned above, 0.01 to 1 part by weight of niobium as $Nb_2O_5$, 0.2 to 1.2 parts by weight of phosphorus as $P_2O_5$, 0.5 to 5 parts by weight of antimony as $Sb_2O_3$, and 0.3 to 1.2 parts by weight of at least one member selected from the group consisting of potassium, cesium, rubidium, and thallium as oxide and the latter-stage catalyst being obtained by using as a catalytic substance the aforementioned at least one member selected from the group consisting of potassium, cesium, rubidium, and thallium of the former-stage catalyst substance in an amount in the range between 17 and 63% by weight as oxide based on the amount of the one member in the former-stage catalyst and subsequently feeding the reaction vessel with the mixture of ortho-xylene and naphthalene and the molecular oxygen-containing gas at a temperature in the range between 300° and 450° C.

In accordance with the method contemplated by this invention, the otherwise possible occurrence of abnormal hot spots can be prevented over a wide range of mixing ratios of ortho-xylene to naphthalene by dividing the catalyst bed proportionately to the bed height ratio as described above and adjusting the activity of the catalyst by fixing the ratio of the content of the component selected from among potassium, cesium, rubidium, and thallium in the latter-stage catalyst to that in the former-stage catalyst in a range between 17 and 63% (hereinafter referred to "alkali ratio").

This method allows phthalic anhydride to be produced stably without sacrificing high productivity from a mixture comprising of ortho-xylene and naphthalene in a widely variable ratio. If the situation of supply of raw materials is notably varied, therefore, this method enables phthalic anhydride of high quality to be obtained inexpensively. As described above, the method of this invention deserves to be called a highly useful method for the production of phthalic anhydride.

Compliance with this invention allows repression of the occurrence of phthalide due to the use of ortho-xylene in a proportion of not less than 50% and the occurrence of naphthoquinone due to the use of ortho-xylene in a proportion of not less than 50% and ensures the production of phthalic anhydride in a high yield.

DESCRIPTION OF THE PREFERRED EMBODIMENTS

Figure 1:
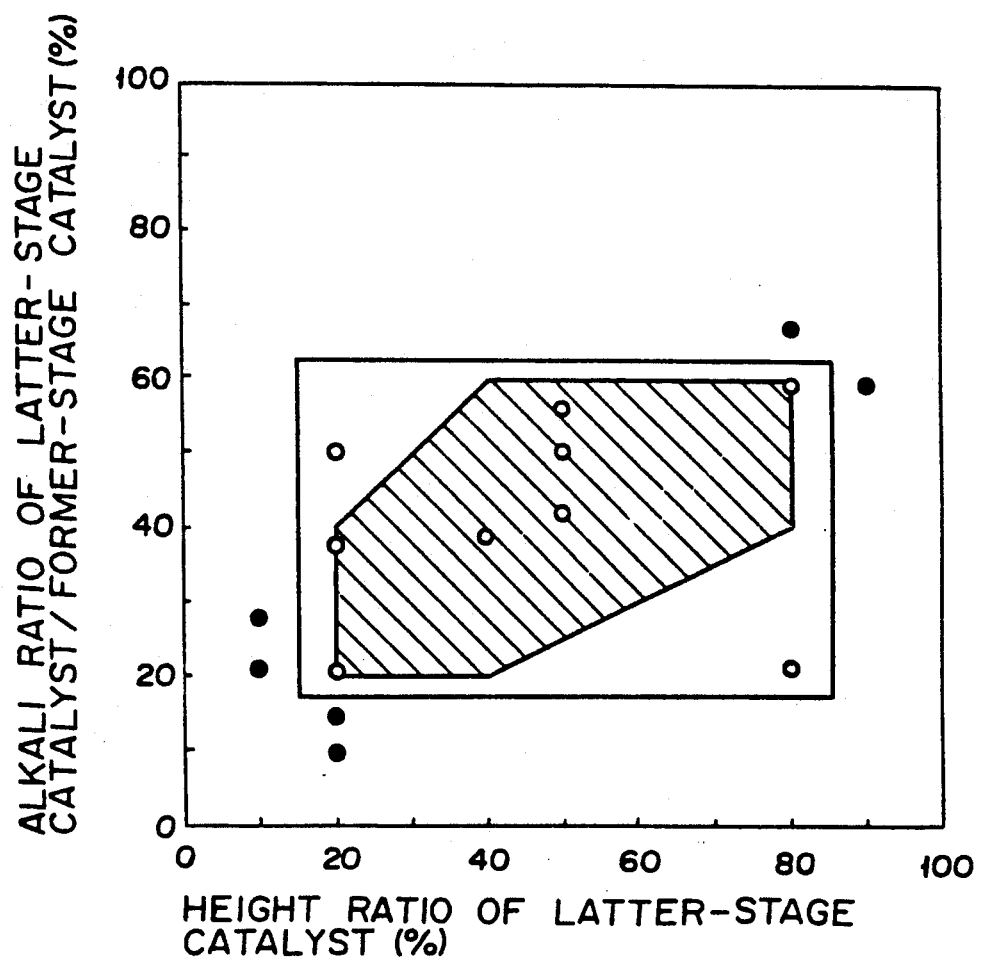
FIG. 1 is graph showing the relationship between height ratio (%) of latter-stage catalyst and alkali and/or thallium ratio of latter-stage catalyst/former-stage catalyst.

Now, this invention will be described more specifically below.

When a shell-and-tube type fixed-bed reaction vessel prepared for use is to be packed with a catalyst, a former-stage catalyst is packed in a bed height of 15 to 85% preferably 20 to 80% of the total catalyst bed height from the raw material gas inlet side and a latter-stage in a bed height of 85 to 15%, preferably 80 to 20% of the total catalyst bed height from the raw material gas outlet side.

When these bed heights for the two stages of catalyst deviate from the respectively defined ranges mentioned above, the load is exerted exclusively on one of the two catalysts and the allowable mixing ratio of ortho-xylene and naphthalene is limited to a narrow range. The catalytic substances to be used in this invention will be described below.

Besides vanadium oxide, the source of vanadium oxide can be suitably selected from among such compounds as ammonium salts, nitrates, sulfates, halides, organic acid salts, and hydroxides which are converted by heating into corresponding oxides. The anatase type titanium dioxide to be used herein have particle diameters substantially in the range between 0.4 and 0.7 μm, preferably between 0.45 and 0.6 μm. The specific surface area, i.e. BET (Brunauer-Emmet-Teller) surface area, of the titanium dioxide is in the range between 10 and 60 $m^2/g$, preferably between 15 and 40 $m^2/g$. The produced catalyst is deficient in activity if the specific surface area of the anatase type titanium dioxide is less than 10 $m^2/g$. The catalyst suffers from inferior durability and from an early decline in yield if this specific surface area exceeds 60 $m^2/g$.

The titanium dioxide endowed with these properties is produced by a method known as the sulfuric acid solution method. It is produced by treating ilmenite ($FeOTiO_2$) with sulfuric acid. Specifically, it is produced by carrying out this treatment with sulfuric acid of a concentration lower than that of sulfuric acid used in the sulfuric acid solidification method, generally of the order of 70 to 80%, then hydrolyzing the product of this treatment at a temperature in the region of 150° C. under increased pressure, and further calcining the resultant hydrolyzate. Owing to the particular nature of the ore used as the source therefor, the titanium dioxide to be used in this invention may possibly contain such extraneous constituents as iron, zinc, aluminum, manganese, chromium, calcium, and lead. So long as the total content of these extraneous constituents is not more than 0.5% by weight as oxide, based on the amount of titanium oxide ($TiO_2$), these constituents do not pose any problem from the standpoint of catalytic performance.

As respects the contents of vanadium oxide and anatase type titanium dioxide in the former-stage catalyst, this catalyst is required to have a vanadium oxide content in the range between 1 and 20 parts by weight, preferably between 2 and 15 parts by weight, as $V_2O_5$ and an anatase type titanium dioxide content in the range between 99 and 80 parts by weight, preferably between 98 and 85 parts by weight, as $TiO_2$.

The content of niobium is in the range between 0.01 and 1 part by weight, preferably between 0.015 and 0.8 part by weight, as $Nb_2O_5$ based on the total amount of vanadium oxide and titanium dioxide taken as 100 parts by weight. The content of phosphorus is in the range between 0.2 and 1.2 parts by weight, preferably between 0.25 and 1 part by weight, as $P_2O_5$ based on the total amount of vanadium oxide and titanium dioxide taken as 100 parts by weight. The content of antimony is in the range between 0.5 and 5 parts by weight, preferably between 1 and 4 parts by weight, as $Sb_2O_3$ based on the total amount of vanadium oxide and titanium dioxide taken as 100 parts by weight.

The content of at least one member selected from the group consisting of potassium, cesium, rubidium, and thallium is in the range between 0.3 and 1.2 parts by weight, preferably between 0.4 and 1.1 parts by weight, as relevant oxide ($K_2O$, $Cs_2O$, $Rb_2O$ and/or $Tl_2O$) based on the total amount of vanadium oxide and titanium dioxide taken as 100 parts by weight. For the inactive carrier to be effectively used in the present invention, it is important that it should maintain stability for a long time at a temperature sufficiently higher than the calcination temperature of the catalyst and the temperature to be assumed by the catalyst during the reaction for the production of phthalic anhydride and that the inactive carrier should not react with the catalytic component. In this sense, it is preferable to use a porous carrier having an alumina ($Al_2O_3$) content of not more than 10% by weight and a silicon carbide (SiC) content of not less than 80% by weight. It is more preferable to use as the inactive carrier a porous carrier having an alumina ($Al_2O_3$) content of not more than 5% by weight and a silicon carbide (SiC) content of not less than 95% by weight and possessing an apparent porosity in the range between 15 and 40%, preferably between 3 and 12%. As a typical inactive carrier, the result of self-sintering silicon carbide (SiC) powder having a purity of not less than 98% can be cited. But this invention does not particularly discriminate against heat-resistant inorganic inactive carriers of a particular shape. The carrier is only required to have an average particle diameter in the range between 2 and 15 mm, preferably between 3 and 12 mm. Typical examples of suitable catalyst shapes are spheres, pellets, cylinders, and rings.

The starting materials for the components, i.e. vanadium, niobium, phosphorus, antimony, potassium, cesium, rubidium, and thallium, which are used in the preparation of the catalyst of this invention are not limited to the oxides of relevant components represented by the formulas $V_2O_5$, $Nb_2O_5$, $P_2O_5$, $Sb_2O_3$, $K_2O$, $Cs_2O$, $Rb_2O$, and $TiO_2$ but may be suitably selected from such substances as ammonium salts, nitrates, sulfates, halides, organic acid salts, and hydroxides of the relevant metals which are converted by heating into the oxides cited above or oxides resembling them.

The method for supporting the catalytically active substance on the inactive carrier is not particularly restricted. The method which comprises placing a specific volume of the inactive carrier in an externally heatable rotary drum and keeping the carrier rotating in the drum at a temperature in the range between 200° and 300° C. while spraying a slurry containing the catalytically active substance onto the carrier in motion thereby supporting the sprayed substance on the carrier is most convenient. In this case, though the amount of the catalytically active substance to be supported on the inactive carrier is variable with the size and shape of the inactive carrier particles to be used, it is preferable that it is in the range between 3 and 30 g, preferably between 5 and 20 g, per 100 ml of the inactive carrier where the inactive carrier is in the form of spheres or cylinders.

After the catalytically active substance has been supported on the heat-resistant inactive carrier as described above, the resultant catalyst composite is calcined under a current of air at a temperature in the range between 450° and 700° C., preferably between 500° and 600° C., for a period in the range between 2 to 10 hours, preferably between 4 and 8 hours, to produce a catalyst required at by this invention.

The latter-stage catalyst to be used in this invention is identical to the former-stage catalyst except that the content of at least one component selected from the group consisting of potassium, cesium, rubidium, and thallium accounts for a proportion in the range between 17 and 63% by weight, preferably between 20 and 60% by weight, based on the amount of the same component used in the former-stage catalyst. The activity of the latter-stage catalyst becomes predominant if this content is less than 17% by weight, whereas the activity of the former-stage catalyst becomes predominant if the content is not less than 63% by weight. In either case, the mixing ratio of ortho-xylene and naphthalene is limited to a narrow range.

Further, the relationship between a layer height ratio (%) of latter-stage catalyst and weight ratio (%) of an alkali component of K, Cs, Rb and/or Tl as oxide in the latter-stage catalyst to the alkali component of K, Cs, Rb and/or Tl as oxide in the former-stage catalyst is as mentioned above and it can be illustrated in a graph in FIG. 1, by the range which satisfies the following formulas:

$$20 \leq y \leq 60$$

$$20 \leq x \leq 80$$

$$0.5x \leq y \leq x + 20$$

wherein x is a layer height ratio (%) of latter-stage catalyst and y is a weight ratio (%) of the component of K, Cs, Rb and/or Tl as oxide in the latter-stage catalyst to the component of K, Cs, Rb and/or Tl as an oxide in the former-stage catalyst. These relationship can be illustrated by a shaded potion of the graph in FIG. 1.

Now, the method contemplated by this invention for the production of phthalic anhydride will be shown below.

The catalytic vapor-phase oxidation of the mixture of ortho-xylene and naphthalene with a molecular oxygen-containing gas by the use of the catalyst described above for the production of phthalic anhydride can be carried out under the following reaction conditions. A tube having an inside diameter in the range between 15 and 40 mm, preferably between 15 and 27 mm, is packed with the catalyst to a height in the range between 1 and 5 m, preferably between 1.5 and 3 m. In this case, the height ratio of the former-stage catalyst to the latter-state catalyst is in the range between 15:85 and 85:15, preferably between 20:80 and 80:20.

The reaction tube is kept heated with a heat transfer medium at a temperature in the range between 300° and 400° C., preferably between 330° and 380° C., and the raw material or the mixture of ortho-xylene and naphthalene can be passed accompanied by air or a gas containing 5 to 21% by volume of molecular oxygen at a concentration in the range between 5 and 70 g of raw material/$Nm^3$ in case of air, and between 5 and 120 g of raw material/$Nm^3$ in case of the molecular oxygen-containing gas, through the reaction tube at a space velocity in the range between 1,000 and 6,000 $hr^{-1}$ (STP; standard temperature pressure), preferably between 1,000 and 4,000 $hr^{-1}$ (STP) The weight ratio of ortho-xylene to naphthalene in the raw material gas is in the range between 1:99 and 99:1 , preferably 5:95 and 95:5, most preferably 10:90 and 90:10.

Now, this invention will be described more specifically below with reference to working examples.

PREPARATION OF CATALYST

Catalyst Preparation 1

An aqueous titanium sulfate solution was obtained by mixing ilmenite and 80% concentrated sulfuric acid, causing them to react thoroughly with each other, and then diluting the product of reaction with water. Iron pieces were added as a reducing agent to the aqueous solution to induce reduction of the iron content in the ilmenite into ferrous ions. The resultant mixture was cooled and ferrous sulfate was precipitated and separated. Steam heated to 150° C. was blown into the resultant aqueous titanium sulfate solution to bring about precipitation of hydrated titanium dioxide. The precipitate separated was washed with water, washed with an acid, washed again with water, and calcined under a current air stream at a temperature of 800° C. for 4 hours. The solid resulting from the calcination was pulverized with a jet air stream to obtain porous anatase type titanium dioxide having an average particle diameter of about 0.5 μm and a BET specific surface area of 22 $m^2/g$.

An aqueous oxalic acid solution obtained by dissolving 250 g of oxalic acid in 6,400 ml of deionized water and 121.87 g of ammonium metavanadate, 9.21 g of ammonium dihydrogen phosphate, 15.41 g of niobium chloride, 20.38 g of cesium sulfate, 0.79 g of potassium sulfate, and 37.89 g of antimony trioxide were added thereto and thoroughly stirred. 1,800 g of the above mentioned titanium dioxide ($TiO_2$) were added to the resultant solution and this suspension was stirred by an emulsifying machine to prepare a catalyst slurry.

In an externally heatable rotary furnace of stainless steel measuring 35 cm in diameter and 80 cm in length, 2,000 ml of a self-sintered SiC carrier in the form of spheres 6 mm in diameter and having an apparent porosity of 35% and a purity of 98.5 % was preheated to a temperature in the range between 200° and 250° C. To the carrier, rotated in a rotary furnace, the catalyst slurry mentioned above was sprayed to support the catalytically active substance on the carrier at a rate of 8.0 g/100 ml of carrier. Then, the catalyst composite consequently obtained was calcined with air in an electric furnace at a temperature of 560° C. for 6 hours. The catalyst thus produced is designated as catalyst (A) hereinafter.

Catalyst preparation 2

A catalyst (B) was produced by following the procedure used for the production of the catalyst (A), except that the amount of cesium sulfate was changed to 13.86 g.

Catalyst preparation 3

A catalyst (C) was produced by following the procedure used for the production of the catalyst (A), except that the amount of cesium sulfate was changed to 13.04 g.

Catalyst preparation 4

A catalyst (D) was produced by following the procedure used for the production of the catalyst (A), except that the amount of cesium sulfate was changed to 10.60 g.

Catalyst preparation 5

A catalyst (E) was produced by following the procedure used for the production of the catalyst (A), except that the amount of cesium sulfate was changed to 7.34 g and that of potassium sulfate to 0.39 g.

Catalyst preparation 6

A catalyst (F) was produced by following the procedure used for the production of the catalyst (E), except that the amount of cesium sulfate was changed to 6.33 g.

Catalyst preparation 7

A catalyst (G) was produced by following the procecure used for the production of the catalyst (E), except that the amount of cesium sulfate was changed to 5.71

Catalyst preparation 8

A catalyst (H) was produced by following the procedure used for the production of the catalyst (E), except that the amount of cesium sulfate was changed to 5.30 g.

Catalyst preparation 9

A catalyst (I) was produced by following the procedure used for the production of the catalyst (E), except that the amount of cesium sulfate was changed to 4.08 g.

Catalyst preparation 10

A catalyst (J) was produced by following the procedure used for the production of the catalyst (A), except that the amount of cesium sulfate was changed to 2.04 g and that of potassium sulfate to 0.20 g.

Catalyst preparation 11

An aqueous titanium sulfate solution was obtained by mixing ilmenite and 80% concentrated sulfuric acid, causing them to react thoroughly with each other, and diluting the product of this reaction with water. Iron pieces were added as a reducing agent to the aqueous solution to induce reduction of the iron content in the ilmenite into ferrous ions. The resultant mixture was cooled and ferrous sulfate was a precipitated and separated. Steam heated to 150° C. was blown into the aqueous titanium sulfate solution consequently obtained to bring about precipitation of hydrated titanium dioxide. The separated precipitate was washed with water, washed with an acid, and washed again with water and the cleaned precipitate was calcined under a current of air at a temperature of 700° C. for 4 hours. The solid product of this calcination was pulverized with a jet air stream, to produce a porous anatase type titanium dioxide having an average particle size of about 0.45 μm and a BET specific surface area of 33 $m^2/g$.

An aqueous oxalic acid solution obtained by dissolving 520 g of oxalic acid in 6,400 ml of deionized water and 257.27 g of ammonium metavanadate, 12.97 g of ammonium dihydrogen phosphate, 16.26 g of niobium chloride, 28.53 g of cesium sulfate, 1.18 g of potassium sulfate, 0.72 g of rubidium sulfate, and 40.00 g of antimony trioxide were added thereto and were thoroughly stirred. The above mentioned 1,800 g of $TiO_2$ added to the resaltant solution and this suspension was stirred by an emulsifying machine, to produce a catalyst slurry. In an externally heated rotary furnace of stainless steel measuring 35 cm in diameter and 80 cm in length, 2,000 ml of a self-sintered SiC carrier in the form of spheres 6 mm in diameter having an apparent porosity of 35% and a purity of 98.5 % by weight were preheated to a temperature in the range between 200° and 250° C. The carrier was kept rotating in the furnace and the catalyst slurry was sprayed thereon to support the catalytically active substance at a rate of 8.0 g/100 ml of carrier. Thereafter, the resultant catalyst composite was calcined with air in an electric furnace at a temperature of 560° C. for 6 hours. The catalyst consequently produce is designated as Catalyst (K) hereinafter.

Catalyst preparation 12

A catalyst (L) was produced by following the procedure used for the production of the catalyst (K), except that the amount of cesium sulfate was changed to 16.30 g, that of potassium sulfate to 0.39 g, and that of rubidium sulfate to 0.36 g.

Catalyst preparation 13

A catalyst (M) was produced by following the procedure used for the production of the catalyst (K), except that the amount of cesium sulfate was changed to 8.15 g, that of potassium sulfate to 0.20 g, and that of rubidium sulfate to 0.12 g.

Catalyst preparation 14

A catalyst (N) was produced by following the procedure used for the production of the catalyst (M), except that the amount of cesium sulfate was changed to 4.08 g.

Catalyst preparation 15

An aqueous titanium sulfate solution was obtained by mixing ilmenite and 80% concentrated sulfuric acid, causing them to react thoroughly with each other, and then diluting the product of this reaction with water. Iron pieces were added as a reducing agent to the aqueous solution to induce reduction of the iron contents in the ilmenite into ferrous ions. The resultant mixture was cooled and ferrous sulfate was precipitated and separated. Steam heated to 150° C. was blown into the aqueous titanium sulfate solution consequently obtained to bring about precipitation of hydrated titanium dioxide. The separated precipitate was washed with water, washed with an acid, and washed again with water and the cleaned precipitate was calcined under a current of air at a temperature of 800° C. for 4 hours. The calcined precipitate was pulverized with a jet air stream to produce a porous anatase type titanium dioxide having an average particle diameter of about 0.5 μm and a BET specific surface area of 22 m²/g.

An aqueous oxalic acid solution obtained by dissolving 250 g of oxalic acid in 6,400 ml of deionized water and 121.87 g of ammonium metavanadate, 9.21 g of ammonium dihydrogen phosphate, 15.41 g of niobium chloride, 8.15 g of cesium sulfate, 6.00 g of thallium nitrate, and 37.89 g of antimony trioxide were added thereto and were thoroughly stirred. The above mentioned 1,800 g of the titanium dioxide ($TiO_2$) were added to the resultant solution and this suspension was stirred by an emulsifying machine to produce a catalyst slurry.

In an externally heatable rotary furnace of stainless steel measuring 35 cm in diameter and 80 cm in length, 2,000 ml of a self-sintered SiC carrier in the form of spheres having an apparent porosity of 35% and a purity of 98.5 % by weight was preheated to a temperature in the range between 200° and 250° C. The carrier was kept rotating in the rotary furnace and the catalyst slurry was sprayed thereon to support the catalytically active substance at a ratio of 8.0 g/100 ml of carrier. Thereafter, the resultant catalyst composite was calcined with air in an electric furnace at a temperature of 560° C. for 6 hours. The catalyst thus obtained is designated as Catalyst (0) hereinafter.

Catalyst preparation 16

A catalyst (P) was produced by following the procedure used for the production of the catalyst (0), except that the amount of cesium sulfate was changed to 4.08 g and that of thallium nitrate to 3.00 g.

The compositions of the catalysts (A) to (P) are collectively shown in Table 1 and Table 2, as divided into former-stage catalysts and latter-stage catalysts.

TABLE 1

| Kind of catalyst | Catalytic composition (weight ratio) | | | | | | | | | Titanium dioxide | |
|---|---|---|---|---|---|---|---|---|---|---|---|
| | $V_2O_5$ | $TiO_3$ | $Sb_2O_3$ | $Nb_2O_5$ | $P_2O_5$ | $Cs_2O$ | $K_2O$ | $Rb_2O$ | $Tl_2O$ | Average particle diameter (μm) | Specific surface area (m²/g) |
| A | 5 | 95 | 2.0 | 0.4 | 0.3 | 0.84 | 0.02 | — | — | 0.5 | 22 |
| B | 5 | 95 | 2.0 | 0.4 | 0.3 | 0.57 | 0.02 | — | — | 0.5 | 22 |
| C | 5 | 95 | 2.0 | 0.4 | 0.3 | 0.54 | 0.02 | — | — | 0.5 | 22 |
| D | 5 | 95 | 2.0 | 0.4 | 0.3 | 0.44 | 0.02 | — | — | 0.5 | 22 |
| K | 10 | 90 | 2.0 | 0.4 | 0.4 | 1.11 | 0.03 | 0.03 | — | 0.45 | 33 |
| O | 5 | 95 | 2.0 | 0.4 | 0.3 | 0.34 | — | — | 0.25 | 0.5 | 22 |

TABLE 2

| Kind of catalyst | Catalytic composition (weight ratio) | | | | | | | | | Titanium dioxide | |
|---|---|---|---|---|---|---|---|---|---|---|---|
| | $V_2O_5$ | $TiO_3$ | $Sb_2O_3$ | $Nb_2O_5$ | $P_2O_5$ | $Cs_2O$ | $K_2O$ | $Rb_2O$ | $Tl_2O$ | Average particle diameter (μm) | Specific surface area (m²/g) |
| E | 5 | 95 | 2.0 | 0.4 | 0.3 | 0.30 | 0.01 | — | — | 0.5 | 22 |
| F | 5 | 95 | 2.0 | 0.4 | 0.3 | 0.27 | 0.01 | — | — | 0.5 | 22 |

TABLE 2-continued

| Kind of catalyst | Catalytic composition (weight ratio) | | | | | | | | Titanium dioxide | |
|---|---|---|---|---|---|---|---|---|---|---|
| | $V_2O_5$ | $TiO_3$ | $Sb_2O_3$ | $Nb_2O_5$ | $P_2O_5$ | $Cs_2O$ | $K_2O$ | $Rb_2O$ | $Tl_2O$ | Average particle diameter ($\mu$m) | Specific surface area ($m^2/g$) |
| G | 5 | 95 | 2.0 | 0.4 | 0.3 | 0.23 | 0.01 | — | — | 0.5 | 22 |
| H | 5 | 95 | 2.0 | 0.4 | 0.3 | 0.22 | 0.01 | — | — | 0.5 | 22 |
| I | 5 | 95 | 2.0 | 0.4 | 0.3 | 0.17 | 0.01 | — | — | 0.5 | 22 |
| J | 5 | 95 | 2.0 | 0.4 | 0.3 | 0.08 | 0.005 | — | — | 0.5 | 22 |
| L | 10 | 90 | 2.0 | 0.4 | 0.4 | 0.64 | 0.01 | 0.01 | — | 0.45 | 33 |
| M | 10 | 90 | 2.0 | 0.4 | 0.4 | 0.32 | 0.005 | 0.005 | — | 0.45 | 33 |
| N | 10 | 90 | 2.0 | 0.4 | 0.4 | 0.16 | 0.005 | 0.005 | — | 0.45 | 33 |
| P | 5 | 95 | 2.0 | 0.4 | 0.3 | 0.17 | — | — | 0.13 | 0.5 | 22 |

OXIDATION REACTION

Example 1

In a reaction tube of iron, 25 mm inside diameter and 3 m in length immersed in a molten salt bath, first the catalyst (I) was packed as a latter-stage catalyst to a height of 0.5 m in the raw material gas outlet part and then the catalyst (A) was packed as a former-stage catalyst to a height of 2.0 m in the raw material gas inlet part.

A mixture comprising ortho-xylene and naphthalene in a weight ratio of 1:1 was mixed with a synthetic gas containing of 21% by volume of oxygen and 79% by volume of nitrogen in a ratio of 70 g/Nm³ (synthetic gas) to produce a mixed gas. The mixed gas was introduced at a space velocity (SV) of 3,000 hr⁻¹ (STP) into the reaction vessel immersed in the molten salt bath maintained at a temperature of 360° C. through the upper inlet thereof to perform oxidation of the mixture of ortho-xylene and naphthalene.

The reaction temperature was adjusted so as to keep the amounts of the by-products phthalide and naphthoquinone produced respectively below 0.1% by weight and 0.3% by weight and the yield of phthalic anhydride was determined. Then, the mixing ratio of ortho-xylene to naphthalene was set at 1:9 or 9:1 and the ratio of the mixture to the synthetic gas was set at 70 g/Nm³. The reaction temperature was adjusted so as to keep the amounts of the by-products phthalide and naphthoquinone produced respectively below 0.1% by weight and 0.3% by weight and the yield of produced phthalic anhydride was determined.

Example 2

In the same reaction tube as used in Example 1, first the catalyst (H) was packed as a latter-stage catalyst to a height of 1.0 m in the raw material gas outlet part and then the catalyst (B) was packed as a former-stage catalyst to a height of 1.5 m in the raw material gas inlet part. Under the same reaction conditions in the same procedure as used in Example 1, the reaction was carried out to determine the yield of produced phthalic anhydride with the mixing ratio of ortho-xylene to naphthalene fixed at 1:1, 1:9, and 9:1. Then, the reaction was continued for 1 year with the mixing ratio of ortho-xylene to naphthalene fixed at 1:1 to conduct the same determination at intervals of three months.

Example 3

In the same reaction tube as used in Example 1, first the catalyst (G) was packed as a latter-stage catalyst to a height of 1.25 m in the raw material gas outlet part and then the catalyst (C) was packed as a former-stage catalyst to a height of 1.25 m in the raw material gas inlet part. Under the same reaction conditions in the same procedure as used in Example 1, the reaction was carried out to determine the yield of produced phthalic anhydride with the mixing ratio of ortho-xylene to naphthalene fixed at 1:1, 1:9, and 9:1.

Example 4

In the same reaction tube as used in Example 1, first the catalyst (F) was packed as a latter-stage catalyst to a height of 2.0 m in the raw material gas outlet part and then the catalyst (D) was packed as a former-stage catalyst to a height of 0.5 m in the raw material gas inlet part. Under the same reaction conditions in the same procedure as used in Example 1, the reaction was carried out to determine the yield of produced phthalic anhydride with the mixing ratio of ortho-xylene to naphthalene fixed at 1:1, 1:9, and 9:1.

Control 1

In the same reaction tube as used in Example 1, first the catalyst (I) was packed as a latter-stage catalyst to a height of 0.25 m in the raw material gas outlet part and then the catalyst (A) was packed as a former-stage catalyst to a height of 2.25 m in the raw material gas inlet part. Under the same reaction conditions in the same procedure as used in Example 1, the reaction was carried out to determine the yield of produced phthalic anhydride with the mixing ratio of ortho-xylene to naphthalene fixed at 1:1, 1:9, and 9:1.

Control 2

In the same reaction tube as used in Example 1, first the catalyst (J) was packed as a latter-stage catalyst to a height of 0.5 m in the raw material gas outlet part and then the catalyst (A) was packed as a former-stage catalyst to a height of 2.0 m in the raw material gas inlet part. Under the same reaction conditions in the same procedure as used in Example 1, the reaction was carried out to determine the yield of produced phthalic anhydride with the mixing ratio of ortho-xylene to naphthalene fixed at 1:1, 1:9, and 9:1.

Control 3

In the same reaction tube as used in Example 1, first the catalyst (F) was packed as a latter-stage catalyst to a height of 2.25 m in the raw material gas outlet part and then the catalyst (D) was packed as a former-stage catalyst to a height of 0.25 m in the raw material gas inlet part. Under the same reaction conditions in the same procedure as used in Example 1, the reaction was carried out to determine the yield of phthalic anhydride with the mixing ratio of ortho-xylene to naphthalene fixed at 1:1, 1:9, and 9:1.

Control 4

In the same reaction tube as used in Example 1, first the catalyst (E) was packed as a latter-stage catalyst to a height of 2.0 m in the raw material gas outlet part and then the catalyst (D) was packed as a former-stage catalyst to a height of 0.5 m in the raw material gas inlet part. Under the same reaction conditions in the same procedure as used in Example 1, the reaction was carried out to determine the yield of produced phthalic anhydride with the mixing ratio of ortho-xylene to naphthalene fixed at 1:1, 1:9, and 9:1.

Example 5

In the same reaction tube as used in Example 1, first the catalyst (P) was packed as a latter-stage catalyst to a height of 1.25 m in the raw material gas outlet part and then the catalyst (O) was packed as a former-stage catalyst to a height of 1.25 m in the raw material gas inlet part. Under the same reaction conditions in the same procedure as used in Example 1, the reaction was carried out to determine the yield of produced phthalic anhydride with the mixing ratio of ortho-xylene to naphthalene fixed at 1:1, 1:9, and 9:1.

Example 6

In the same reaction tube as used in Example 1, first tho catalyst (P) was packed as a latter-stage catalyst to a height of 0.5 m in the raw material gas outlet part and then the catalyst (O) was packed as a former-stage catalyst to a height of 2.0 m in the raw material gas inlet part. Under the same reaction conditions in the same procedure as used in Example 1, the reaction was carried out to determine the yield of produced phthalic anhydride with the mixing ratio of ortho-xylene to naphthalene fixed at 1:1, 1:9, and 9:1.

Example 7

In the same reaction tube as used in Example 1, first the catalyst (I) was packed as a latter-stage catalyst to a height of 2.0 m in the raw material gas outlet part and then the catalyst (A) was packed as a former-stage catalyst to a height of 0.5 m in the raw material gas inlet part. Under the same reaction conditions in the same procedure as used in Example 1, the reaction was carried out to determine the yield of produced phthalic anhydride with the mixing ratio of ortho-xylene to naphthalene fixed at 1:1, 1:9, and 9:1.

The results of the oxidation reaction in Examples 1 to 7 and Controls 1 to 4 are shown in Table 3. The conditions of the reaction performed with an oxygen content of 21% by volume are indicated as Reaction Conditions 1 in the table.

TABLE 3

| | Reaction condition | Former-catalyst | Latter-stage catalyst | Layer height ratio *** | component ratio* | Initial phthalic anhydride yield** Ortho-xylene/Ortho-naphthalene | | | Phthalic anhydride yeild after 1 year** Ortho-xylene/naphthalene | | |
|---|---|---|---|---|---|---|---|---|---|---|---|
| | | | | | | 10/90 | 50/50 | 90/10 | 10/90 | 50/50 | 90/10 |
| Example 1 | 1 | (A) | (I) | 80:20 | 1:0.21 | 105.0 | 107.5 | 110.0 | — | — | — |
| Example 2 | 1 | (B) | (H) | 60:40 | 1:0.39 | 104.5 | 108.0 | 111.5 | 103.5 | 103.5 | 110.5 |
| Example 3 | 1 | (C) | (G) | 50:50 | 1:0.42 | 103.0 | 107.0 | 111.0 | — | — | — |
| Example 4 | 1 | (D) | (F) | 20:80 | 1:0.59 | 99.5 | 106.5 | 108.0 | — | — | — |
| Control 1 | 1 | (A) | (I) | 90:10 | 1:0.21 | 98.5 | 106.0 | 103.0 | — | — | — |
| Control 2 | 1 | (A) | (J) | 80:20 | 1:0.10 | 100.5 | 105.5 | Reaction is difficult | — | — | — |
| Control 3 | 1 | (D) | (F) | 10:90 | 1:0.59 | Reaction is difficult | 104.5 | Reaction is difficult | — | — | — |
| Control 4 | 1 | (D) | (E) | 20:80 | 1:0.67 | Reaction is difficult | 105.5 | Reaction is difficult | — | — | — |
| Example 5 | 1 | (O) | (P) | 50:50 | 1:0.50 | 104.5 | 107.0 | 110.3 | — | — | — |
| Example 6 | 1 | (O) | (P) | 80:20 | 1:0.50 | 99.0 | 106.0 | 108.0 | — | — | — |
| Example 7 | 1 | (A) | (I) | 20:80 | 1:0.21 | 99.5 | 105.5 | 107.0 | — | — | — |

*Content ratio (by weight) of K, Cs, Rb and/or Tl as oxide (latter-stage catalyst/former-stage catalyst)
**Phthalic anhydride yield when yield of phthalide is not more than 0.1% by weight and yeild of naphthoquinone is not more than 0.3% by weight.
***Former-stage catalyst layer:latter-stage catalyst layer.

Example 8

In a reaction tube of iron, 25 mm inside diameter and 3 m in length immersed in a molter salt bath, first the catalyst (M) was packed as a latter-stage catalyst to a height of 0.5 m in the raw material gas outlet part and then the catalyst (K) was packed as a former-stage catalyst to a height of 2.0 m in the raw material gas inlet part. A mixture comprising ortho-xylene and naphthalene in a ratio of 1:1 was mixed with a synthetic gas containing 10% by volume of oxygen, 10% by volume of steam, and 80% by weight volume of nitrogen in a ratio of 85 g/Nm$^3$ (synthetic gas) to produce a mixed gas. This mixed gas was introduced at a space velocity (SV) of 2,500 hr$^{-1}$ (STP) into the reaction tube immersed in the molten salt bath kept at a temperature of 355° C. through the upper inlet thereof to perform oxidation reaction of the mixture of ortho-xylene and naphthalene. With the reaction temperature adjusted so as to keep the amounts of the by-products phthalide and naphthoquinone produced respectively below 0.1% by weight and 0.3% by weight, the reaction was carried out to determine the yield of produced phthalic anhydride. Then, the mixing ratio of ortho-xylene to naphthalene was fixed at 1:9 or 9:1 and the ratio of the mixture to the synthetic gas was fixed at 85 g/Nm$^3$. With the reaction temperature adjusted so as to keep the amounts of by-produced phthalide and naphthoquinone respectively below 0.1% by weight and 0.3% by weight, the reaction was carried out to determine the yield of produced phthalic anhydride.

Example 9

In the same reaction tube as used in Example 8, first the catalyst (L) was packed as a latter-stage catalyst to a height of 1.25 m in the raw material gas outlet part and then the catalyst (K) was packed as a former-stage catalyst to a height of 1.25 m in the raw material gas inlet part. Under the same reaction conditions in the same procedure as used in Example 8, the reaction was carried out to determine the yield of phthalic anhydride with the mixing ratio of ortho-xylene to naphthalene fixed at 1:1, 1:9, and 9:1. Then the reaction was continued for 1 year with the mixing ratio of ortho-xylene to naphthalene fixed at 1:1 to conduct the same determination at intervals of 3 months.

Control 5

In the same reaction tube as used in Example 8, first the catalyst (M) was packed as a latter-stage catalyst to a height of 0.25 m in the raw material gas outlet part and then the catalyst (K) was packed as a former-stage catalyst to a height of 2.25 m in the raw material gas inlet part. Under the same reaction conditions in the same procedure as used in Example 8, the reaction was carried out with the mixing ratio of ortho-xylene to naphthalene fixed at 1:1, 1:9, and 9:1 to determine the yield of produced phthalic anhydride.

Control 6

In the same reaction tube as used in Example 8, first the catalyst (N) was packed as a latter-stage catalyst to a height of 0.50 m in the raw material gas outlet part and then the catalyst (K) was packed as a former-stage catalyst to a height of 2.0 m in the raw material gas inlet part. Under the same reaction conditions in the same procedure as used in Example 8, the reaction was carried out with the mixing ratio of ortho-xylene to naphthalene fixed at 1:1, 1:9, and 9:1 to determine the yield of produced phthalic anhydride.

The results of the test obtained in Examples 8 and 9 and Controls 5 and 6 are shown in Table 4. The conditions of the reaction performed with the oxygen content fixed at 10% by volume are indicated as Reaction Conditions 2 in the table.

dioxide as $TiO_2$ having particle diameters substantially in the range between 0.4 and 0.7 μm and a specific surface area (BET surface area) in the range between 10 and 60 m$^2$/g and further incorporating therein, based on 100 parts by weight of the total amount of said two components, 0.01 to 1 parts by weight of niobium as $Nb_2O_5$, 0.2 to 1.2 parts by weight of phosphorus as $P_2O_5$, 0.5 to 5 parts by weight of antimony as $Sb_2O_3$, and 0.3 to 1.2 parts by weight of at least one member selected from the group consisting of potassium, cesium, rubidium, and thallium as oxide and said latter-stage catalyst being obtained by using as a catalytic substance said at least one member selected from the group consisting of potassium, cesium, rubidium, and thallium of said former-stage catalyst in an amount in the range between 17 and 63% by weight as oxide based on the amount of said one member in said former-stage catalyst and subsequently feeding said reaction vessel with said mixture of ortho-xylene and naphthalene and said molecular oxygen-containing gas at a temperature in the range between 300° and 450° C.

2. A method according to claim 1, wherein said inactive carrier is a porous carrier having an alumina ($Al_2O_3$) content of not more than 10% by weight and a silicon carbide (SiC) content of not less than 80% by weight.

3. A method according to claim 2, wherein said inactive carrier is a porous carrier having an apparent porosity in the range between 15 and 40%.

4. A method according to claim 1, wherein the weight ratio of ortho-xylene to naphthalene in said raw material gas is in the range between 1:99 and 99:1.

5. A method according to claim 1, wherein the amount of said at least one member selected from the group consisting of potassium, cesium, rubidium, and thallium as oxide in said latter-stage catalyst is in the range between 20 and 60 % by weight, based on the

TABLE 4

| | Reaction condition | Former-catalyst | Latter-stage catalyst | Layer height ratio*** | component ratio* | Initial phthalic anhydride yield** xylene/Ortho-naphthalene | | | Phthalic anhydride yeild after 1 year** Ortho- xylene/naphthalene | | |
|---|---|---|---|---|---|---|---|---|---|---|---|
| | | | | | | 10/90 | 50/50 | 90/10 | 10/90 | 50/50 | 90/10 |
| Example 8 | 2 | (K) | (M) | 80:20 | 1:0.28 | 103.5 | 108.0 | 110.0 | — | — | — |
| Example 9 | 2 | (K) | (L) | 50:50 | 1:0.56 | 102.5 | 109.0 | 111.5 | 101.5 | 108.5 | 109.5 |
| Control 5 | 2 | (K) | (M) | 90:10 | 1:0.28 | 99.5 | 104.0 | Reaction is difficult | — | — | — |
| Control 6 | 2 | (K) | (N) | 80:20 | 1:0.15 | 100.0 | 105.0 | Reaction is difficult | — | — | — |

*Content ratio (by weight) of K, Cs, Rb and/or Tl as oxide (latter-stage catalyst/former-stage catalyst)
**Phthalic anhydride yield when yield of phthalide is not more than 0.1% by weight and yield of naphthoquinone is not more than 0.3% by weight.
***Former-stage catalyst layer:latter-stage catalyst layer.

What is claimed is:

1. A method for the production of phthalic anhydride by the catalytic vapor-phase oxidation of a mixture of ortho-xylene and naphthalene with a molecular oxygen-containing gas by the use of a shell-and-tube type fixed-bed reactor, which method comprises packing in said reactor a former-stage catalyst in a bed height of 15 to 85% by volume of the total catalyst bed height from the raw material gas inlet side and a latter-stage catalyst in a bed height of 85 to 15% by volume of the total catalyst bed height from the raw material gas outlet side in the form of superposed layers, said former-stage catalyst being obtained by supporting a catalyst substance on an inactive carrier at a ratio in the range between 5 and 20 g/100 ml, said catalytic substance comprising 1 to 20 parts by weight of vanadium oxide as $V_2O_5$ and 99 to 80 parts by weight of a porous anatase type titanium amount of the same component in said former-stage catalyst.

6. A method according to claim 1, wherein the height ratio of said former-stage catalyst to said latter-stage catalyst is in the range between 20:80 and 80:20.

7. A method according to claim 2, wherein said inactive carrier has an alumina content of not more than 5% by weight and a silicon carbide content of not less than 95% by weight.

8. A method according to claim 1, wherein the reaction is carried out at a temperature in the range between 300° and 400° C. at a space velocity in the range between 1,000 and 6000 hr$^{-1}$.

9. A method according to claim 1, wherein the reaction is carried out at a temperature in the range between 330° and 380° C. at a space velocity in the range between 1,000 and 4,000 hr$^{-1}$.

10. A method according to claim 1, wherein the surface area of said anatase type titanium oxide is in the range between 15 and 40 m$^2$/g.

11. A method according to claim 2, wherein vanadium oxide accounts for a proportion in the range between 2 and 15 parts by weight as V$_2$O$_5$ and anatase type titanium dioxide for a proportion in the range between 98 and 85 parts by weight as TiO$_2$ and, based on the total amount of vanadium oxide and titanium dioxide taken as 100 parts by weight, niobium accounts for a proportion in the range between 0.015 and 0.8 parts by weight as Nb$_2$O$_5$, phosphorus for a proportion in the range between 0.25 and 1 parts by weight as P$_2$O$_5$, antimony for a proportion in the range between 1 and 4 parts by weight as Sb$_2$O$_3$, and said at least one component selected from the group consisting of potassium, cesium, rubidium, and thallium for a proportion in the range between 0.4 and 1.1 parts by weight as oxide.

12. A method according to claim 1, wherein a relationship between a layer height ratio (%) of latter-stage catalyst and weight ratio (%) of at least one component selected from the group consisting of potassium, cesium, rubidium, and thallium as an oxide in the latter-stage catalyst to said at least one component in the former-stage catalyst is in the range of the following formulas:

$$20 \leq y \leq 60$$

$$20 \leq x \leq 80$$

$$0.5\,x \leq y \leq x + 20$$

wherein x is a layer height ratio (%) of latter-stage catalyst and y is a weight (%) ratio of the component in the latter-stage catalyst/the component in the former-stage catalyst.

* * * * *